United States Patent [19]

Braun et al.

[11] 4,087,520
[45] May 2, 1978

[54] LOWERING BLOOD PRESSURE WITH NEW L-3-(3,4-DIHYDROXYPHENYL)-2-METHYL-ALANINE PEPTIDES

[75] Inventors: Franz Braun, Rimbach, Austria; Kurt Stach, deceased, late of Mannheim-Waldhof, Germany; by Werner Plattner, executor, Linz, Austria; Max Thiel, Mannheim, Germany; Gisbert Sponer, Hemsbach, Germany; Karl Dietmann, Mannheim-Vogelstang, Germany

[73] Assignee: Boehringer Mannheim GmbH, Mannheim-Waldhof, Germany

[21] Appl. No.: 665,341

[22] Filed: Mar. 9, 1976

[30] Foreign Application Priority Data

Mar. 12, 1975 Germany .............................. 2510634

[51] Int. Cl.$^2$ ..................... A61K 37/00; C07C 103/52
[52] U.S. Cl. ..................... 424/177; 260/112.5 R; 260/519; 424/309
[58] Field of Search ..................... 260/112.5 R, 519; 424/177, 309

[56] References Cited

U.S. PATENT DOCUMENTS

| 3,803,120 | 4/1974 | Felix | 260/112.5 R |
| 3,891,696 | 6/1975 | Bodor et al. | 260/112.5 R |

OTHER PUBLICATIONS

Moyer et al., Chem. Abstr. 66; 9914y (1967).
Ebihara et al., Chem. Abstr. 72, 109438m (1970).

*Primary Examiner*—Delbert R. Phillips
*Attorney, Agent, or Firm*—Burgess, Dinklage & Sprung

[57] ABSTRACT

An L-3-(3,4-dihydroxyphenyl)-2-methyl-alanine peptide of the formula

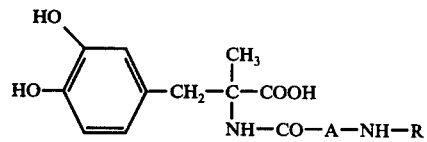

wherein
A is an alkylene radical which can be substituted by a hydroxyl group or by a phenyl radical which optionally carries at least one hydroxyl group, and
R is a hydrogen atom or a lower alkyl radical or a glycyl or alanyl radical, or a pharmacologically compatible salt thereof. These compounds are outstanding in lowering blood pressure.

13 Claims, No Drawings

LOWERING BLOOD PRESSURE WITH NEW L-3-(3,4-DIHYDROXYPHENYL)-2-METHYL-ALANINE PEPTIDES

The present invention is concerned with new L-3-(3,4-dihydroxyphenyl)-2-methyl-alanine peptides and with the preparation thereof.

The L-3-(3,4-dihydroxyphenyl)-2-methyl-alanine peptides according to the present invention are compounds of the general formula

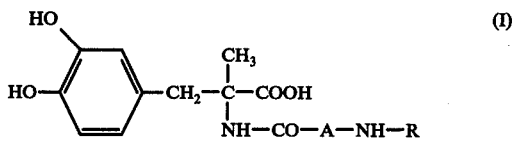

wherein
- A is an alkylene radical which can be substituted by a hydroxyl group or by a phenyl radical which optionally carries at least one hydroxyl group, and
- R is a hydrogen atom or a lower alkyl radical or a glycyl or alanyl radical, or a pharmacologically compatible salt thereof.

All the carbon atoms of the radicals A and R with a center of asymmetry can have the L- or D-configuration, the L-configuration being preferred. The present invention concerns not only the racemic mixtures but also the pure L- and D-enantiomers.

The alkylene radical A can contain up to 5 carbon atoms and the lower alkyl radical R can contain up to 3 carbon atoms, the methyl radical being preferred.

The new compounds of general formula (I) and the pharmacologically compatible salts thereof have blood pressure-lowering properties.

The new compounds of general formula (I) according to the present invention can be prepared by condensing L-3-(3,4-dihydroxyphenyl)-2-methyl-alanine of the formula:

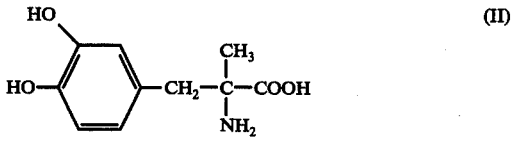

the hydroxyl and/or carboxy groups of which can, if desired, be temporarily protected, with a carboxylic acid of the general formula:

HOOC-A-Z    (III)

in which A has the same meaning as above and Z is a reactive residue or an —NHR group in which R has the same meaning as above, wherein, if desired, a hydroxyl group present in the alkylene radical A, as well as the —NHR group, can be temporarily protected, and, when Z is a reactive residue, this is subsequently exchanged for an —NHR group and any protective groups present are subsequently split off in known manner, whereafter the compound obtained is, if desired, converted into a pharmacologically-compatible salt.

The preparation of the compounds (I) according to the present invention takes place according to methods which are conventional in peptide chemistry. It is preferable to operate in the presence of inert solvents, for example dioxane, and of agents splitting off water, for example N,N'-dicyclohexylcarbodiimide, at ambient temperature.

The intermediate protective groups for the hydroxyl substituents in the compounds of general formulae (II) and (III) can be those conventionally used for hydroxyl groups, for example benzyl or benzyloxycarbonyl groups.

The carboxy group of the L-3-(3,4-dihydroxyphenyl)-2-methyl-alanine of formula (II) can be protected, for example, by esterification, preferably with a lower aliphatic alcohol or with benzyl alcohol.

The —NHR group can be temporarily protected with conventional amino protective groups, for example with a benzyloxycarbonyl group.

The reactive derivatives of the carboxylic acids of general formula (III) are preferably acid halides, acid anhydrides or carboxylic acid esters.

Reactive residues Z in compounds of general formula (III) are, in particular, acid radicals, for example of hydrohalic acids or sulfonic acids.

The compounds according to the present invention of general formula (I) have an amphoteric character. Therefore, they can form pharmacologically compatible salts not only with acids but also with bases. For the preparation of acid-addition salts, the compounds according to the present invention are reacted, preferably in an organic solvent, with an equivalent amount of a pharmacologically compatible inorganic or organic acid, for example, hydrochloric acid, hydrobromic acid, phosphoric acid, sulfuric acid, acetic acid, citric acid, maleic acid, benzoic acid, or the like. The carboxylic acid group can be neutralized, for example, by reaction with an alkali metal or alkaline earth metal base, with ammonia or with an organic amine.

For the preparation of pharmaceutical compositions, at least one of the new compounds according to the present invention is mixed in known manner with an appropriate pharmaceutical carrier or diluent and optionally with an aroma, flavoring and/or coloring material and then formed, for example, into tablets or dragees or, with the addition of appropriate adjuvants, suspended or dissolved in water or in an oil, for example olive oil.

Preferred according to the present invention, apart from the compounds mentioned in the following Examples, is glycyl-glycyl-L-3-(3,4-dihydroxyphenyl)-2-methyl-alanine.

The following Examples are given for the purpose of illustrating the present invention:

EXAMPLE 1

Glycyl-L-3-(3,4-dihydroxyphenyl)-2-methyl-alanine

Variant I:

11.25 g (0.05 mole) L-3-(3,4-dihydroxyphenyl)-2-methyl-alanine methyl ester (m.p. 164° – 166° C; $[\alpha]_D^{20}$ = $-6.3°$ (c=1 g/100 ml in 1N hydrochloric acid)) are suspended in 250 ml anhydrous dioxane in a 500 ml three-necked flask equipped with a stirrer and a calcium chloride tube. 12.52 g (0.06 mole) benzyloxycarbonylglycine and 10.3 g (0.05 mole) N,N'-dicyclohexylcarbodiimide are successively added thereto and the reaction mixture stirred at ambient temperature, with the exclusion of moisture. After only a few minutes, N,N'-dicyclohexylurea starts to crystallize out.

After stirring for a further 4 hours and then leaving to stand for 16 hours at ambient temperature, the urea derivative is filtered off with suction (10.0 g, 89.4% of theory) and the filtrate is evaporated in a vacuum. The very viscous residue obtained is taken up in 150 ml ethyl acetate and successively washed four times with 20 ml amounts of approximately 5% aqueous sodium bicarbonate solution, four times with 20 ml amounts of 1N hydrochloric acid and then twice with 30 ml amounts of water. The ethyl acetate phase, which contains the desired reaction product, is, after drying over anhydrous sodium sulfate, evaporated in a vacuum. There are obtained 20.82 g (100.0% of theory) benzyloxycarbonyl-glycyl-L-3-(3,4-dihydroxyphenyl)-2-methyl-alanine methyl ester in the form of a colorless amorphous powder which, according to thin layer chromatographic testing, is only slightly contaminated.

For complete purification, the crude product can be dissolved in 100 ml of a chloroform-methanol mixture (15:1) and chromatographed on a column (90 × 5.5 cm) of silica gel 60 (70 - 230 mesh, Merck), using the same solvent mixture: yield 17.5 g (84.1% of theory) of colorless, amorphous powder.

For the hydrolysis of the methyl ester group, 10.4 g. (0.025 mole) benzyloxycarbonyl-glycyl-L-3-(3,4-dihydroxyphenyl)-2-methyl-alanine methyl ester are placed in a three-necked flask equipped with a stirrer, dropping funnel and a gas inlet. After complete removal of the air by passing through a weak current of nitrogen, 95 ml 1N aqueous sodium hydroxide solution are allowed to run in through the dropping funnel and the solution then stirred for 30 minutes at ambient temperature. 95 ml 1N hydrochloric acid are then added dropwise. The crude hydrolysis product separates out as a very viscous oil which is taken up in 100 ml ethyl acetate and, for further purification, is extracted three times from the ethyl acetate solution with 30 ml amounts of 10% aqueous sodium bicarbonate solution. The free carboxylic acid is separated out from the combined aqueous extracts by careful acidification with 1N hydrochloric acid. The free acid obtained is taken up in about 100 ml ethyl acetate and dried with anhydrous sodium sulfate. After completely distilling off the solvent in a vacuum, there are obtained 9.0 g (89.5% of theory) of thin layer chromatographically uniform benzyloxycarbonylglycyl-L-3-(3,4-dihydroxyphenyl)-2-methyl-alanine in the form of a colorless, amorphous foam.

For the hydrogenolysis of the benzyloxycarbonyl group, 2.5 g palladium oxide in 130 ml. methanol are prehydrogenated at ambient temperature and atmospheric pressure. A solution of 20.12 g. (0.05 mole) benzyloxycarbonylglycyl-L-3-(3,4-dihydroxyphenyl)-2-methyl-alanine in 170 ml methanol is then added thereto and hydrogenation carried out at ambient temperature in the usual manner for 4 hours by passing through hydrogen until the splitting off of carbon dioxide is complete. The catalyst is then filtered off with suction and the solvent is distilled off in a vacuum. There are obtained 13.45 g (100% of theory) of a colorless, amorphous crude product which is taken up in 28 ml water and cooled to 0° C. From the solution there crystallize out 11.88 g of thin layer chromatographically and analytically pure glycyl-L-3-(3,4-dihydroxyphenyl)-2-methyl-alanine dihydrate; m.p. 187° C.; $[\alpha]_D^{20} = -8.0°$ (c = 1g/100 ml in water).

Variant II:

In a 2 liter four-necked flask equipped with a stirrer, 2 dropping funnels, a gas inlet, pH electrode and thermometer, 45 g (0.2 mole) L-3-(3,4-dihydroxyphenyl)-2-methyl-alanine methyl ester are mixed with 300 ml water and 500 ml chloroform and cooled to 0° C, while stirring vigorously. 12.34 g (0.11 mole) chloroacetyl chloride dissolved in 12 ml chloroform are then added thereto dropwise over the course of 1 hour. After a further 45 minutes, a weak current of nitrogen is passed in for the displacement of the air and 14.8 g (0.13 mole) chloroacetyl chloride dissolved in 15 ml chloroform and a solution of 36.96 g (0.26 mole) sodium carbonate in 118 ml water added dropwise and alternatingly at 0° C over the course of 1.25 hours (pH of the solution 7.5 – 8.5). The reaction mixture is further stirred for 1.5 hours, without cooling. The unreacted methyl ester (20.0 g = 44.4% of theory) is then filtered off with suction and the chloroform solution separated off and evaporated to dryness. There are obtained 33.0 g (54.8% of theory) N-chloroacetyl-L-3-(3,4-dihydroxyphenyl)-2-methyl-alanine methyl ester in the form of a yellowish viscous oil.

b 30.17 g. (0.1 mole) of this methyl ester are hydrolyzed, in an atmosphere of nitrogen, in 305 ml. 1N aqueous sodium hydroxide solution for 1 hour at ambient temperature, then neutralized with about 77 ml 4N hydrochloric acid. The oil which separates out is extracted twice with 150 ml amounts of ethyl acetate. The extracts are combined, dried with anhydrous sodium sulfate and then evaporated in a vacuum. There are obtained 26.1 g. (9.10% of theory) N-chloroacetyl-L-3-(3,4-dihydroxyphenyl)-2-methyl-alanine in the form of a yellowish oil.

28.7 g (0.1 mole) N-chloroacetyl-L-3-(3,4-dihydroxyphenyl)-2-methyl-alanine are dissolved, under an atmosphere of nitrogen, in 260 ml concentrated ammonia solution and left to react for 5 days at ambient temperature. The reaction mixture is then evaporated in a vacuum and the crude product purified by column chromatography (column 60 × 6.4 cm; silica gel 60, Merck; elution agent: n-butanol-glacial acetic acid-water 2:1:1). The thin layer chromatographically pure eluate gives, after evaporation in a vacuum and recrystallization of the residue from 35 ml. water, 22.8 g (75.0% of theory) glycyl-L-3-(3,4-dihydroxyphenyl)-2-methyl-alanine dihydrate; m.p. 186° – 187° C.

EXAMPLE 2

L-Alanyl-L-3-(3,4-dihydroxyphenyl)-2-methyl-alanine 11.25 g. (0.05 mole) L-3-(3,4-dihydroxyphenyl)-2-methyl-alanine methyl ester and 13.38 g (0.06 mole) benzyloxycarbonyl-L-alanine (m.p. 84° – 86° C; $[\alpha]_D^{20} = -15.6°$ (c=2 g/100 ml in acetic acid) are reacted with 10.3 g (0.05 mole) N,N'-dicyclohexylcarbodiimide in the same manner as described in Example 1 (I) and then worked up. There are obtained 21.5 g (100% of theory) of colorless crude product which, after column chromatographic purification, give 16.51 g (76.9% of theory) pure benzyloxycarbonyl-L-alanyl-L-3-(3,4-dihydroxyphenyl)-2-methyl-alanine methyl ester.

10.75 g (0.025 mole) benzyloxycarbonyl-L-alanyl-L-3-(3,4-dihydroxyphenyl)-2-methyl-alanine methyl ester are hydrolyzed, in the manner described in Example 1 (I), with 95 ml. 1N aqueous sodium hydroxide solution for 50 minutes at ambient temperature. There are obtained 9.46 g (91.0% of theory) of thin layer chromatographically homogeneous benzyloxycarbonyl-L-alanyl-L-3-(3,4-dihydroxyphenyl)-2-methyl-alanine in the form of a colorless foam.

20.8 g. (0.05 mole) benzyloxycarbonyl-L-alanyl-L-3-(3,4-dihydroxyphenyl)-2-methyl-alanine are, for the hydrogenolysis of the benzyloxycarbonyl group, hydrogenated in the manner described in Example 1 (I) for 1.5 hours at ambient temperature. There are obtained 13.38 g (94.7% of theory) of crude product which, after recrystallization from 13.5 ml water, give 11.7 g analytically pure L-alanyl-L-3-(3,4-dihydroxyphenyl)-2-methyl-alanine trihydrate; m.p. 82° - 87° C (in a sealed tube); $[\alpha]_D^{20} = -26.9°$ (c = 1 g/100 ml in water).

EXAMPLE 3

D-Alanyl-L-3-(3,4-dihydroxyphenyl)-2-methyl-alanine.

15.75 g. (0.07 mole) L-3-(3,4-dihydroxyphenyl)-2-methyl-alanine methyl ester and 16.83 g (0.075 mole) benzyloxycarbonyl-D-alanine (m.p. 84° - 86° C; $[\alpha]_D^{20} = +14.8°$ (c=2 g/100 ml in water)) are reacted in 350 ml of dioxane with 14.4 g (0.07 mole) N,N'-dicyclohexylcarbodiimide in the manner described in Example 1 (I) and then worked up. There are obtained 30.1 g (100% of theory) of colorless crude product. The column chromatographic purification thereof gives 29.1 g (96.6% of theory) of thin layer chromatographically pure benzyloxycarbonyl-D-alanyl-L-3-(3,4-dihydroxyphenyl)-2-methyl-alanine methyl ester in the form of a colorless powder.

10.75 g. (0.025 mole) benzyloxycarbonyl-D-alanyl-L-3-(3,4-dihydroxyphenyl)-2-methyl-alanine methyl ester are hydrolyzed, in the manner described in Example 1 (I), with 95 ml 1N aqueous sodium hydroxide solution for 2 hours at ambient temperature and then worked up. There are obtained 9.46 g (91.0% of theory) of thin layer chromatographically homogeneous benzyloxycarbonyl-D-alanyl-L-3-(3,4-dihydroxyphenyl)-2-methyl-alanine in the form of a colorless foam.

The hydrogenolysis of the benzyloxycarbonyl group is carried out, in the manner described in Example 1 (I), with 20.8 g (0.05 mole) benzyloxycarbonyl-D-alanyl-L-3-(3,4-dihydroxyphenyl)-2-methyl-alanine and then worked up. There are obtained 14.05 g (99.6% of theory) of crude product which is recrystallized from about 20 ml water. There are obtained 8.35 g colorless, analytically pure D-alanyl-L-3-(3,4-dihydroxyphenyl)-2-methyl-alanine monohydrate; m.p. about 205° C; $[\alpha]_D^{20} = +33.7°$ (c.=1 g/100 ml in water).

EXAMPLE 4

L-N-Methyl-alanyl-L-3-(3,4-dihydroxyphenyl)-2-methyl-alanine 15.75 g (0.07 mole) L-3-(3,4-dihydroxyphenyl)-2-methyl-alanine methyl ester and 18.79 g. (0.077 mole) benzyloxycarbonyl-L-N-methyl-alanine (oil; $[\alpha]_D^{20} = -24.8°$ (c.=1 g/100 ml in dimethyl formamide)) are reacted in 350 ml anhydrous dioxane with 14.42 g (0.07 mole) N,N'-dicyclohexylcarbodiimide in the manner described in Example 1 (I) and then worked up. There are obtained 29.21 g (94.0% of theory) of colorless crude product. Column chromatographic purification (elution agent: chloroform:methanol 20:1) gives 14.18 g (46.5% of theory) thin layer chromatographically pure benzyloxycarbonyl-L-N-methyl-alanyl-L-3-(3,4-dihydroxyphenyl)-2-methyl-alanine methyl ester in the form of an amorphous powder.

11.1 g (0.025 mole) benzyloxycarbonyl-L-N-methylalanyl-L-3-(3,4-dihydroxyphenyl)-2-methyl-alanine methyl ester are hydrolyzed, in the manner described in Example 1 (I), for 1.5 hours at ambient temperature and then worked up. There are obtained 9.20 g (85.5% of theory) of powdery, thin layer chromatographically homogeneous benzyloxycarbonyl-L-N-methyl-alanyl-L-3-(3,4-dihydroxyphenyl)-2-methyl-alanine.

The hydrogenolysis of the benzyloxycarbonyl group is carried out with a solution of 10.27 g (0.025 mole) benzyloxycarbonyl-L-N-methyl-alanyl-L-3-(3,4-dihydroxyphenyl)-2-methyl-alanine in 90 ml methanol and 30 ml water, in a manner analogous to that described in Example 1 (I), with 1.25 g palladium oxide in 100 ml methanol and the reaction mixture then worked up. There are obtained 7.11 g (96.0% of theory) of crude product which is purified by column chromatography (column 90 × 3 cm; silica gel 60, 70 - 230 mesh, Merck; elution agent: acetone-water 4:1). The thin layer chromatographically pure eluate is evaporated in a vacuum and the residue obtained is dissolved in a little water, slowly precipitated out with ethanol and then evaporated to dryness. There are thus obtained 5.69 g (76.8% of theory) of powdery L-N-methyl-alanyl-L-3-(3,4-dihydroxyphenyl)-2-methyl-alanine which, after drying at ambient temperature, still contains 0.95 mol water and 0.63 mole ethanol; $[\alpha]_D^{20} = +38.9°$ (c.=1 g/100 ml in methanol).

EXAMPLE 5

β-Alanyl-L-3-(3,4-dihydroxyphenyl)-2-methyl-alanine 15.75 g (0.07 mole) L-3-3,4-dihydroxyphenyl)-2-methyl-alanine methyl ester and 17.20 g. (0.077 mole) benzyloxycarbonyl-β-alanine (m.p. 106° C.) are reacted in 350 ml dioxane with 14.4 g (0.07 mole) N,N'-dicyclohexylcarbodiimide in the manner described in Example 1 (I) and the reaction mixture then worked up. There is obtained a crude yield of 27.8 g. (92.4% of theory) of colorless powder. Column chromatographic purification gives 15.15 g (50.3% of theory) of thin layer chromatographically pure benzyloxycarbonyl-β-alanyl-L-3-(3,4-dihydroxyphenyl)-2-methyl-alanine methyl ester.

10.75 g (0.025 mole) benzyloxycarbonyl-β-alanyl-L-3-(3,4-dihydroxyphenyl)-2-methyl-alanine methyl ester are hydrolyzed, in the manner described in Example 1 (I), for 1.5 hours at ambient temperature and then worked up. There are obtained 8.90 g. (85.6% of theory) of thin layer chromatographically pure benzyloxycarbonyl-β-alanyl-L-3-(3,4-dihydroxyphenyl)-2-methyl-alanine in the form of a colorless foam.

The hydrogenolysis of the benzyloxycarbonyl group is carried out with a solution of 12.49 g (0.03 mole) benzyloxycarbonyl-β-alanyl-L-3-(3,4-dihydroxyphenyl)-2-methyl-alanine in 110 ml methanol and 40 ml water, using 1.5 g palladium oxide in 100 ml methanol in the manner described in Example 1 (I). The catalyst is filtered off with suction and well washed out with 200 ml water and the filtrate is evaporated in a vacuum. There are obtained 7.88 g (92.9% of theory) of crystalline crude product. This is recrystallized from 100 ml water to give 6.64 g (78.4% of theory) of colorless analytically pure β-alanyl-L-3-(3,4-dihydroxyphenyl)-2-methyl-alanine dihydrate; m.p. 147° C; $[\alpha]_D^{20} = -37.7°$ (c =1 g/100 ml in acetic acid).

EXAMPLE 6

L-Seryl-L-3-(3,4-dihydroxyphenyl)-2-methyl-alanine 14.63 g (0.065 mole) L-3-(3,4-dihydroxyphenyl-2-methyl-alanine methyl ester and 22.39 g (0.068 mole) N-benzyloxycarbonyl-O-benzyl-L-serine are reacted in 325 ml dioxane with 13.36 g (0.065 mole) N,N'-dicyclohexylcarbodiimide in the manner described in Example 1 (I) and the reaction mixture then worked up. There is obtained a crude yield of 34.15 g (100% of theory) of colorless foam. Column chromatographic purification (column: 90 × 4.5 cm; silica gel 60 Merck; elution agent: chloroform-methanol 49:1) gives 21.88 g (64.1% of theory) of thin layer chromatographically pure N-benzyloxycarbonyl-O-benzyl-L-seryl-L-3-(3,4-dihydroxyphenyl)-2-methyl-alanine methyl ester in the form of an amorphous powder.

13.40 g (0.025 mole) N-benzyloxycarbonyl-O-benzyl-L-seryl-L-3-(3,4-dihydroxyphenyl)-2-methyl-alanine methyl ester are dissolved in 100 ml. tetrahydrofuran and hydrolyzed, in the manner described in Example 1 (I), with 50 ml 2N aqueous sodium hydroxide solution for 3 hours at 35° C. The reaction mixture is then neutralized with about 50 ml 2N hydrochloric acid and the tetrahydrofuran completely distilled off in a vacuum. After the addition of about 40 ml water, the crude hydrolysis product is taken up in 100 ml ethyl acetate and further worked up in the manner described in Example 1 (I). There are obtained 10.20 g (78.4% of theory) of thin layer chromatographically pure N-benzyloxycarbonyl-O-benzyl-L-seryl-L-3-(3,4-dihydroxyphenyl)-2-methyl-alanine in the form of a colorless powder.

The hydrogenolysis of the N-benzyloxycarbonyl and O-benzyl groups is carried out in a manner analogous to that described in Example 1 (I) by adding a solution of 13.06 g (0.025 mole) N-benzyloxycarbonyl-O-benzyl-L-seryl-L-3-(3,4-dihydroxyphenyl)-2-methyl-alanine in 150 ml dioxane and 25 ml 1N hydrochloric acid to freshly prehydrogenated palladium (1.25 g palladium oxide in 90 ml dioxane and 30 ml water) and passing hydrogen therethrough for about 6 hours at 25° C. After filtering off the catalyst with suction, the filtrate is neutralized with about 25 ml 1N aqueous sodium hydroxide solution and evaporated to dryness in a vacuum. The residue is dissolved in 70 ml water and cooled to 0° C to bring about crystallization. There are obtained 2.24 g (30.1% of theory) of coloress, analytically and thin layer chromatographically pure L-seryl-L-3-(3,4-dihydroxyphenyl)-2-methyl-alanine which, after drying in a vacuum dessicator, still contains 2.3 moles water; m.p. 196° - 197° C (decomp.); $[\alpha]_D^{20} = -4.4°$ (c=1 g/100 ml in acetic acid).

EXAMPLE 7

L-Leucyl-L-3-(3,4-dihydroxyphenyl)-2-methyl-alanine 16.90 g (0.075 mole) L-3-(3,4-dihydroxyphenyl)-2-methyl-alanine methyl ester and 21.87 g (0.083 mole) benzyloxycarbonyl-L-leucine ($[\alpha]_D^{20} = -18.4°$ (c=1 g/100 ml in acetic acid) in 380 ml dioxane are reacted with 15.45 g (0.075 mole) N,N'-dicyclohexylcarbodiimide in the manner described in Example 1 (I) and the reaction mixture then worked up. There is obtained a crude yield of 35.4 g (100% of theory) of colorless powder. Column chromatographic purification as described in Example 1 (I) gives 21.70 g (61.4% of theory) of thin layer chromatographically pure benzyloxycarbonyl-L-leucyl-L-3-(3,4-dihydroxyphenyl)-2-methyl-alanine methyl ester in the form of an amorphous powder.

18.88 g (0.04 mole) benzyloxycarbonyl-L-leucyl-L-3-(3,4-didydroxyphenyl)-2-methyl-alanine methyl ester are hydrolyzed, in the manner described in Example 1 (I), with 152 ml 1N aqueous sodium hydroxide solution for 2 hours at ambient temperature and the reaction mixture then worked up. There are obtained 14.32 g (78.2% of theory) of thin layer chromatographically homogeneous benzyloxycarbonyl-L-leucyl-L-3-(3,4-dihydroxyphenyl)-2-methyl-alanine in the form of an amorphous powder.

The benzyloxycarbonyl group is split off in the manner described in Example 1 (I). 2.0 g palladium oxide are pre-hydrogenated in 110 ml. methanol and 25 ml. water. To this is then added a solution of 18.34 g (0.04 mole) benzyloxycarbonyl-L-leucyl-L-3-(3,4-dihydroxyphenyl)-2-methyl-alanine in 120 ml methanol and 50 ml water, followed by hydrogenation for 2 hours. After working up the reaction mixture, there are obtained 13.0 g (100% of theory) of crude product which is recrystallized from 30 ml water. There are obtained 8.34 g. of colorless thin layer chromatographically and analytically pure L-leucyl-L-3-(3,4-dihydroxyphenyl)-2-methyl-alanine which, after drying in a vacuum desiccator, contains 2.5 moles water; m.p. 106° - 107° C. (in a sealed tube); $[\alpha]_D^{20} = -21.4°$ (c.=1 g/100 ml in water).

EXAMPLE 8

L-Phenylalanyl-L-3-(3,4-dihydroxyphenyl)-2-methyl-alanine

In the manner described in Example 1 (I), 15.78 g (0.07 mole) L-3-(3,4-dihydroxyphenyl)-2-methyl-alanine methyl ester and 23.92 g (0.08 mole) benzyloxycarbonyl-L-phenylalanine (m.p. 85° - 87° C; $[\alpha]_D^{20} = +4.6°$ (c.=1.5 g/100 ml in acetic acid)) are reacted in 350 ml dioxane with 14.42 g (0.07mole) N,N'-dicyclohexylcarbodiimide. There is obtained a crude yield of 35.45 g (100% of theory) of colorless foam. Column chromatographic purification thereof in the manner described in Example 1 (I) gives 33.67 g (95% of theory) benzyloxycarbonyl-L-phenyl-alanyl-L-3-(3,4-dihydroxyphenyl)-2-methyl-alanine methyl ester in the form of an amorphous powder.

20.26 g (0.04 mole) benzyloxycarbonyl-L-phenyl-alanyl-L-3-(3,4-dihydroxyphenyl)-2-methyl-alanine methyl ester are, in the manner described in Example 1 (I), hydrolyzed with 152 ml 1N aqueous sodium hydroxide solution for 3 hours at ambient temperature and the reaction mixture then worked up. There are obtained 16.35 g (83% of theory) benzyloxycarbonyl-L-phenylalanyl-L-3-(3,4-dihydroxyphenyl)-2-methyl-alanine in the form of a yellowish, thin layer chromatographically homogeneous powder.

19.70 g(0.04 mole) benzyloxycarbonyl-L-phenyl-alanyl-L-3-(3,4-dihydroxyphenyl)-2-methyl-alanine are, for the hydrogenolysis of the benzyloxycarbonyl group, hydrogenated in the manner described in Example 1 (I) for 5 hours at ambient temperature using 2.0 g palladium oxide in 230 ml. methanol and the reaction mixture then worked up. There are obtained 14.08 g (98.1% of theory) of crude product. The crude product is dissolved in ethanol and precipitated out again with diethyl ether and thereafter filtered off and dried for 2 hours at 80° C in an oil pump vacuum over phosphorus pentoxide. There are obtained 9.61 g. pure L-phenylalanyl-L-3-(3,4-dihydroxyphenyl)-2-methyl-alanine monohydrate; m.p. 160° - 163° C (decomp.); $[\alpha]_D^{20} = +8.1°$ (c. = 1 g/100 ml in methanol).

EXAMPLE 9

L-Tyrosyl-L-3-(3,4-dihydroxyphenyl)-2-methyl-alanine 9.0 g (0.04 mole) L-3-(3,4-dihydroxyphenyl)-2-methylalanine methyl ester and 22.08 g. (0.063 mole) N-benzyloxycarbonyl-L-tyrosine dihydrate ($[\alpha]_D^{20} = +3.8°$ (c =1.5 in acetic acid)) are reacted in 200 ml dioxane with 11.3 g (0.055 mole) N,N'-dicyclohexylcarbodiimide and then worked up as described in Example 1 (I) and subjected to column chromatography. There are obtained 19.7 g (94.2% of theory) benzyloxycarbonyl-L-tyrosyl-L-3-(3,4-dihydroxyphenyl)-2-methyl-alanine methyl ester in the form of a colorless powder.

20.90 g. (0.04 mole) N-benzyloxycarbonyl-L-tyrosyl-L-3-(3,4-dihydroxyphenyl)-2-methyl-alanine methyl ester are hydrolyzed in the manner described in Example 1 (I) with 192 ml 1N aqueous sodium hydroxide solution for 2.5 hours at ambient temperature and the reaction mixture then worked up. There are obtained 18.20 g (89.5% of theory) of thin layer chromatographically pure benzyloxycarbonyl-L-tyrosyl-L-3-(3,4-dihydroxyphenyl)-2-methyl-alanine in the form of a colorless powder.

The hydrogenolysis of the benzyloxycarbonyl group is carried out in the manner described in Example 1 (I). 1.5 g. palladium oxide are pre-hydrogenated in 100 ml. methanol and 20 ml. water. To this is then added a solution of 15.25 g (0.03 mole)N-benzyloxycarbonyl-L-tyrosyl-L-3-(3,4-dihydroxyphenyl)-2-methyl-alanine in 150 ml methanol and 30 ml water and hydrogenation is carried out for 3 hours. After working up the reaction mixture, there are obtained 10.4 g (92.5% of theory) of colorless crude product which is recrystallized from 20 ml water. There are obtained 8.1 g (72.6% of theory) of thin layer chromatographically and analytically pure L-tyrosyl-L-3-(3,4-dihydroxyphenyl)-2-methylalanine; m.p. 205° C (decomp., upon rapid heating); $[\alpha]_D^{20} = +6.5°$ (c = 1 g/100 ml in methanol).

EXAMPLE 10

L-[3-(3,4-Dihydroxyphenyl)-2-methyl-alanyl]-L-3-(3,4-dihydroxyphenyl)-2-methyl-alanine (a) N-benzyloxycarbonyl-L-3-(3,4-dihydroxyphenyl)-2-methyl-alanine used as starting material can be prepared in the following manner:

In a 1 liter three-necked flask equipped with a stirrer, 2 dropping funnels and a gas inlet, there are placed 23.8 g L-3-(3,4-dihydroxyphenyl)-2-methyl-alanine (water content 11.8%; molecular weight 238). After the complete removal of air by a weak current of nitrogen, 150 ml 2N aqueous sodium hydroxide solution are allowed to run in through a dropping funnel, while cooling with ice, and the solution is cooled to 0° C. Within the course of 25 minutes, with vigorous stirring and ice cooling, there are alternatingly added in small portions a solution of 66 ml benzyl chloroformate in 66 ml toluene and 150 ml 2N aqueous sodium hydroxide solution. After a further 30 minutes stirring, the reaction mixture is weakly acidified with 6N hydrochloric acid and the reaction mixture extracted three times with 200 ml amounts of diethyl ether. The ethereal extract is shaken up three times with 50 ml amounts of 0.5N hydrochloric acid and the ethereal solution, after drying over anhydrous sodium sulfate, is evaporated in a vacuum. There are obtained 59.57 g (97.4% of theory) N-benzyloxycarbonyl-L-3-[3,4-di-(benzyloxycarbonyloxy)-phenyl]-2-methyl-alanine in the form of a yellowish resin which is thin layer chromatographically and analytically pure.

Splitting off of the two O,O'-benzyloxycarbonyl groups is carried out with the apparatus and by the method of working described in Example 1 (I). 12.26 g (0.02 mole) N-benzyloxycarbonyl-L-3-[3,4-di-(benzyloxycarbonyloxy)phenyl]-2-methyl-alanine are dissolved in 550 ml tetrahydrofuran and 890 ml water and hydrolyzed with 160 ml 1N aqueous sodium hydroxide solution for one hour at ambient temperature. The reaction mixture is then neutralized with about 160 ml 1N hydrochloric acid and the tetrahydrofuran distilled off completely in a vacuum. After the addition of about 40 ml water, the crude hydrolysis product is taken up in 100 ml ethyl acetate and further worked up in the manner described in Example 1 (I). There are obtained 5.80 g (84.1% of theory) of thin layer chromatographically pure N-benzyloxycarbonyl-L-3-(3,4-dihydroxyphenyl)-2-methyl-alanine in the form of a very viscous, yellowish oil.

(b) 13.50 g (0.06 mole) L-3-(3,4-dihydroxyphenyl)-2-methyl-alanine methyl ester and 22.80 g (0.066 mole) N-benzyloxycarbonyl-L-3-(3,4-dihydroxyphenyl)-2-methylalanine are reacted in 300 ml dioxane with 12.36 g (0.06 mole) N,N-dicyclohexylcarbodiimide in the manner described in Example 1(I) and the reaction mixture then worked up. Column chromatographic purification of the crude product (column: 90 × 5.5 cm; silica gel 60, Merck; elution agent: chloroform-methanol 10:1) gives 10.62 g (32.1% of theory) of powdery, thin layer chromatographically pure N-benzyloxycarbonyl-L-[3-(3,4-dihydroxyphenyl)-2-methylalanyl]-L-3-(3,4-dihydroxyphenyl)-2-methyl-alanine methyl ester.

22.10 g (0.04 mole) of this ester are hydrolyzed in the manner described in Example 1 (I) with 232 ml. 1N aqueous sodium hydroxide solution for 3.5 hours at ambient temperature and the reaction mixture then worked up. There are obtained 16.5 g (76.7% of theory) thin layer chromatographically homogeneous N-benzyloxycarbonyl-L-[3-(3,4-dihydroxyphenyl)-2-methylalanyl]-L-3-(3,4-dihydroxyphenyl)-2-methyl-alanine (i.e. N-benzyloxycarbonyl-L-α-methyldopyl-L-α-methyl-dopa).

Hydrogenolysis of the benzyloxycarbonyl group is carried out in the manner described in Example 1 (I). 1.25 g palladium oxide are pre-hydrogenated in 100 ml methanol and 30 ml water. To this is then added a solution of 13.46 g (0.025 mole) N-benzyloxycarbonyl-L-α-methyldopyl-L-α-methyl-dopa in 90 ml methanol, followed by hydrogenation for 3 - 4 hours. After working up the reaction mixture, there is obtained a brownish crude product which is purified by column chromatography (column: 90 × 5.5 cm; silica gel 60 Merck; elution agent: acetonewater 8:1). The thin layer chromatographically pure eluate collected is evaporated in a vacuum, taken up in 50 ml water, treated with some charcoal and, after filtration, evaporated to dryness. There are obtained 5.38 g. powdery, analytically pure L-[3-(3,4-dihydroxyphenyl)-2-methylalanyl]-L-3-(3,4-dihydroxyphenyl)-2-methyl-alanine (i.e. L-α-methyldopyl-L-α-methyl dopa) which, after drying in a vacuum desiccator, still contains 2.36 moles of water; $[\alpha]_D^{20} = +34.4°$ (c. = 1 g/100 ml in water).

EXAMPLE 11

L-Alanyl-L-alanyl-L-3-(3,4-dihydroxyphenyl)-2-methylalanine 11.25 g (0.05 mole) L-3-(3,4-dihydroxyphenyl)-2-methyl-alanine methyl ester and 16.18 g (0.055 mole) benzyloxycarbonyl-L-alanyl-L-alanine (m.p. 152° - 153° C; $[\alpha]_D^{20} = -34.5°$ (c = 1 g/100 ml in methanol)) are reacted, in the manner described in Example 1 (I), in 250 ml. dioxan with 10.3 g (0.05 mole) N,N'-dicyclohexylcarbodiimide, whereafter the reaction mixture is worked up and purified. There are obtained 11.76 g (46.9% of theory) powdery, thin layer chromatographically pure benzyloxycarbonyl-L-alanyl-L-alanyl-L-3-(3,4-dihydroxyphenyl)-2-methyl-alanine methyl ester.

12.5 g (0.025 mole) benzyloxycarbonyl-L-alanyl-L-alanyl-L-3-(3,4-dihydroxyphenyl)-2-methyl-alanine methyl ester are hydrolyzed, in the manner described in Example 1 (I), with 190 ml. 0.5N aqueous sodium hydroxide solution for 50 minutes at ambient temperature and the reaction mixture then worked up. There are obtained 4.90 g (40.3% of theory) thin layer chromatographically pure N-benzyloxycarbonyl-L-alanyl-L-alanyl-L-3-(3,4-dihydroxyphenyl)-2-methyl-alanine.

Hydrogenolysis of the benzyloxycarbonyl group is carried out in a manner analogous to that described in Example 1 (I). 1.0 g. palladium oxide are prehydrogenated in 50 ml. methanol and 5 ml. water. To this is added a solution of 9.75 g (0.02 mole) of the N-benzyloxycarbonyltripeptide in 80 ml methanol, followed by hydrogenation for 3 - 4 hours. The colorless crude product obtained is purified by column chromatography (column: 90 × 3.5 cm; silica gel 60 Merck; elution agent: acetone-water 4:1). The thin layer chromatographically pure eluate is evaporated in a vacuum and dried in a desiccator. There are obtained 6.14 g analytically pure L-alanyl-L-alanyl-L-3-(3,4-dihydroxyphenyl)-2-methyl-alanine in the form of a yellowish powder which contains 1.78 mole water; $[\alpha]_D^{20} = +20.5°$ (c = 1 g/100 ml in methanol).

The compounds of the invention constitute potent anti-hypertensive agents. The compounds have proved particularly effective in the treatment of patients with severe or sustained elevation of blood pressure, particularly diastolic pressure. The compounds are suitable for use in almost all forms of fixed and progressive hypertensive disease, including that in which blood pressure is moderately elevated.

The compounds can be administered orally, as pills, tablets, capsules, powders and the like. The preferred form of oral administration is as a tablet containing 100 - 300 mg of active compound.

The compounds can also be administered parenterally. Injection solutions containing 50 mg/ml of injection solution are preferred.

The dosage schedule is entirely dependent on the condition of the patient, his response to the treatment and whether or not he is ambulatory or hospitalized. The treatment should be begun with small doses (100 mg) and increased gradually depending upon the patient's response. The dosage can be increased at 5 to 7 day intervals until an average daily dose of 100-300 mg is reached. For maintenance, two to four doses a day are usually required.

In order to establish the effectiveness of the novel products of the invention as agents for reducing blood pressure, a series of tests as follows were carried out.

The following were the test methods used:

The test animals were rats into which arterial catheters had been implanted in a sterile operation via the arteria femoralis into the aorta. It was possible to measure the animals' blood pressure in the awake state directly in the blood with a transducer (Statham Transducer Type TP 23 D 6) via a carrier frequency measuring bridge. The animals were treated by administration of 10% common salt (sodium chloride) in their feed and, starting on the sixth week of their life, two injections per week of 5 mg at a time of 11-deoxycorticosteroneacetate per animal and thus developed an arterial high pressure in the median with values of 190 to 130 mm Hg. The test compounds were administered to the animals as follows: After the blood pressure control values had been determined, the animals received the test compound perorally suspended in 10 ml of 1% methyl cellusose solution in a dosage of 0.6 millimole/kg and measurements were taken 4 hours after oral application of the substance.

The results are set forth in the Table below. The values set forth in the Table represent in each case the median of at least 6 individual measurements of blood pressure depression (in mm Hg) per applied substance.

TABLE

| Active Material | Blood Pressure Reduction, mm |
|---|---|
| α-Methyl-Dopa | 33 ± 4.9 |
| L-Alanyl-L-alanyl-L-3-(3,4-dihydroxy-phenyl)-2-methyl-alanine | 58 ± 5.8 |
| L-Alanyl-L-3-(3,4-dihydroxy-phenyl)-2-methyl-alanine | 51 ± 6.0 |
| L-Seryl-L-3-(3,4-dihydroxy-phenyl)-2-methyl-alanine | 52 ± 7.5 |
| Glycyl-L-3-(3,4-dihydroxy-phenyl)-2-methyl-alanine | 37 ± 9.1 |
| Control (1% Methylcellulose) | −4 ± 2.5 (rise) |

The present invention also provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative but not limitative of the present invention and that other embodiments within the spirit and scope of the invention will suggest themselves to those skilled in the art.

What we claim is:

1. An L-3-(3,4-dihydroxyphenyl)-2-methyl-alanine peptide of the formula

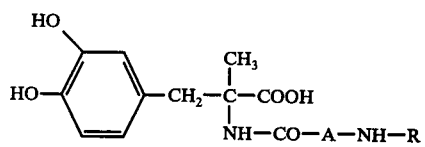

wherein
A is an alkylene radical having up to 5 carbon atoms which can be substituted by a hydroxyl group or by a phenyl radical which optionally carries at least one hydroxyl group, and R is a hydrogen atom or a lower alkyl radical or a glycyl or alanyl radical, or a pharmacologically compatible salt thereof.

2. A peptide or salt thereof according to claim 1, wherein A is an alkylene radical having up to 5 carbon atoms substituted by a hydroxyl group.

3. A peptide or salt thereof according to claim 1, wherein A is an alkylene radical having up to 5 carbon atoms and substituted by a phenyl radical which can carry a hydroxyl group.

4. A peptide or salt thereof according to claim 1, wherein R is a hydrogen atom or an alkyl radical having up to 3 carbon atoms.

5. A peptide or salt thereof according to claim 1, wherein R is a glycyl radical.

6. A peptide or salt thereof according to claim 1, wherein R is an alanyl radical.

7. A peptide or salt thereof according to claim 1, wherein said peptide is glycyl-L-3-(3,4-dihydroxyphenyl)-2-methylalanine.

8. A peptide or salt thereof according to claim 1, wherein said peptide is L-alanyl-L-3-(3,4-dihydroxyphenyl)-2-methylalanine.

9. A peptide or salt thereof according to claim 1, wherein said peptide is L-seryl-L-3-(3,4-dihydroxyphenyl)-2-methylalanine.

10. A peptide or salt thereof according to claim 1, wherein said peptide is L-alanyl-L-alanyl-L-3-(3,4-dihydroxyphenyl)-2-methyl-alanine.

11. A blood pressure-lowering composition, comprising a blood pressure-lowering effective amount of at least one peptide or salt thereof according to claim 1, in admixture with a solid or liquid pharmaceutical diluent or carrier.

12. The method of lowering the blood pressure of a subject which comprises administering to said subject a blood pressure-lowering effective amount of a peptide or salt thereof according to claim 1.

13. The method according to claim 12, wherein said peptide is glycyl-L-3-(3,4-dihydroxyphenyl)-2-methylalanine, L-alanyl-L-3-(3,4-dihydroxyphenyl)-2-methylalanine, L-seryl-L-3-(3,4-dihydroxyphenyl)-2-methylalanine or L-alanyl-L-alanyl-L-3-(3,4-dihydroxyphenyl)-2-methylalanine.

* * * * *